United States Patent
Inoue

(10) Patent No.: US 8,780,445 B2
(45) Date of Patent: Jul. 15, 2014

(54) OPTICAL SYSTEM FOR RIGID SCOPE AND RIGID ENDOSCOPE

(71) Applicant: Olympus Medical Systems Corp., Tokyo (JP)

(72) Inventor: Takahiro Inoue, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/765,075

(22) Filed: Feb. 12, 2013

(65) Prior Publication Data
US 2013/0194667 A1      Aug. 1, 2013

Related U.S. Application Data

(63) Continuation of application No. PCT/JP2012/062590, filed on May 17, 2012.

(30) Foreign Application Priority Data

Aug. 8, 2011    (JP) .................................. 2011-173074

(51) Int. Cl.
*G02B 5/18*    (2006.01)
*A61B 1/06*    (2006.01)

(52) U.S. Cl.
USPC ............................ 359/566; 359/434; 600/160

(58) Field of Classification Search
CPC ........ A61B 1/00163–1/00197; G02B 27/0056; G02B 27/4211
USPC .......... 600/101–183; 359/566–569, 686–692, 359/362–363, 368, 372–376, 434–435, 359/643–647, 656–661, 741–743; 385/117
See application file for complete search history.

(56) References Cited

U.S. PATENT DOCUMENTS

| 7,511,891 B2 | 3/2009 | Messerschmidt | |
| 2002/0018305 A1* | 2/2002 | Kohno | .......................... 359/736 |
| 2004/0125445 A1* | 7/2004 | Hoogland | ..................... 359/435 |
| 2008/0273247 A1* | 11/2008 | Kazakevich | .................. 359/637 |

FOREIGN PATENT DOCUMENTS

| JP | 08-029678 | 2/1996 |
| WO | 01/22866 | 4/2001 |

OTHER PUBLICATIONS

International Search Report, dated Jul. 24, 2012, issued in corresponding Japanese Patent Application No. PCT/JP2012/062590.
E. Ezhov, et al., "Apochromatic Correction of the Rigid Grin Endoscope," Opoelectronics Instrumentation and Data Processing 43(1): 70-75 (2007).

* cited by examiner

*Primary Examiner* — Stephone B Allen
*Assistant Examiner* — Kimberly N Kakalec
(74) *Attorney, Agent, or Firm* — Kenyon & Kenyon LLP

(57) ABSTRACT

By suitably correcting a secondary spectrum, a clear, bright optical image is obtained. Provided is a rigid-scope optical system including: an objective optical system; and at least one relay optical systems that are formed of positive front groups, middle groups, and back groups in this order from an entrance side and that reimage an optical image imaged at imaging planes at the entrance side onto imaging planes at an exit side, wherein axial chromatic aberration between two wavelengths is corrected by an optical system other than the diffractive optical element, and axial chromatic aberration between the two wavelengths and another wavelength is corrected by the diffractive optical element.

5 Claims, 15 Drawing Sheets

OPTICAL SYSTEM FOR RIGID SCOPE AND RIGID ENDOSCOPE

CROSS-REFERENCE TO RELATED APPLICATIONS

This is a continuation of International Application PCT/JP2012/062590, with an international filing date of May 17, 2012, which is hereby incorporated by reference herein in its entirety. This application claims the benefit of Japanese Patent Application No. 2011-173074, the content of which is incorporated herein by reference.

TECHNICAL FIELD

The present invention relates to a rigid-scope optical system and a rigid endoscope.

BACKGROUND ART

In addition to common combined lenses, diffractive optical elements are conventionally used as means for correcting axial chromatic aberrations in optical systems provided in rigid endoscopes (see, for example, PTL 1).

CITATION LIST

Patent Literature

{PTL 1} Japanese Unexamined Patent Application, Publication No. Hei 8-29678

SUMMARY OF INVENTION

Technical Problem

In the optical system described in PTL 1, although the axial chromatic aberration between two wavelengths is corrected by a diffractive optical element, axial chromatic aberration related to wavelengths other than these wavelengths is not corrected and remains as a so-called secondary spectrum. In addition, the optical performance is low because of a simple lens arrangement. In other words, a reduction in diffraction efficiency and flare occur because light beams are incident at an angle with respect to the diffractive surface, NA (numerical aperture) is not sufficient, and a negative secondary spectrum is produced due to over-correction of the secondary spectrum as a result of the inevitable increase in the power distribution of the diffractive surface.

Solution to Problem

A first aspect of the present invention is a rigid-scope optical system including: an objective optical system; and at least one relay optical system that is formed of a positive front group, a middle group, and a back group in this order from an entrance side and that reimages an optical image imaged at a primary imaging plane at the entrance side onto a secondary imaging plane at an exit side; wherein the middle group of one of the relay optical systems is provided with a diffractive optical element having a diffractive surface, and wherein axial chromatic aberration between two wavelengths is corrected by an optical system other than the diffractive optical element, and axial chromatic aberration between the two wavelengths and another wavelength is corrected by the diffractive optical element.

A second aspect of the present invention is a rigid endoscope provided with the rigid-scope optical system mentioned above.

DESCRIPTION OF EMBODIMENTS

A rigid-scope optical system 100 according to an embodiment of the present invention will be described below with reference to FIG. 1.

Figure 1:
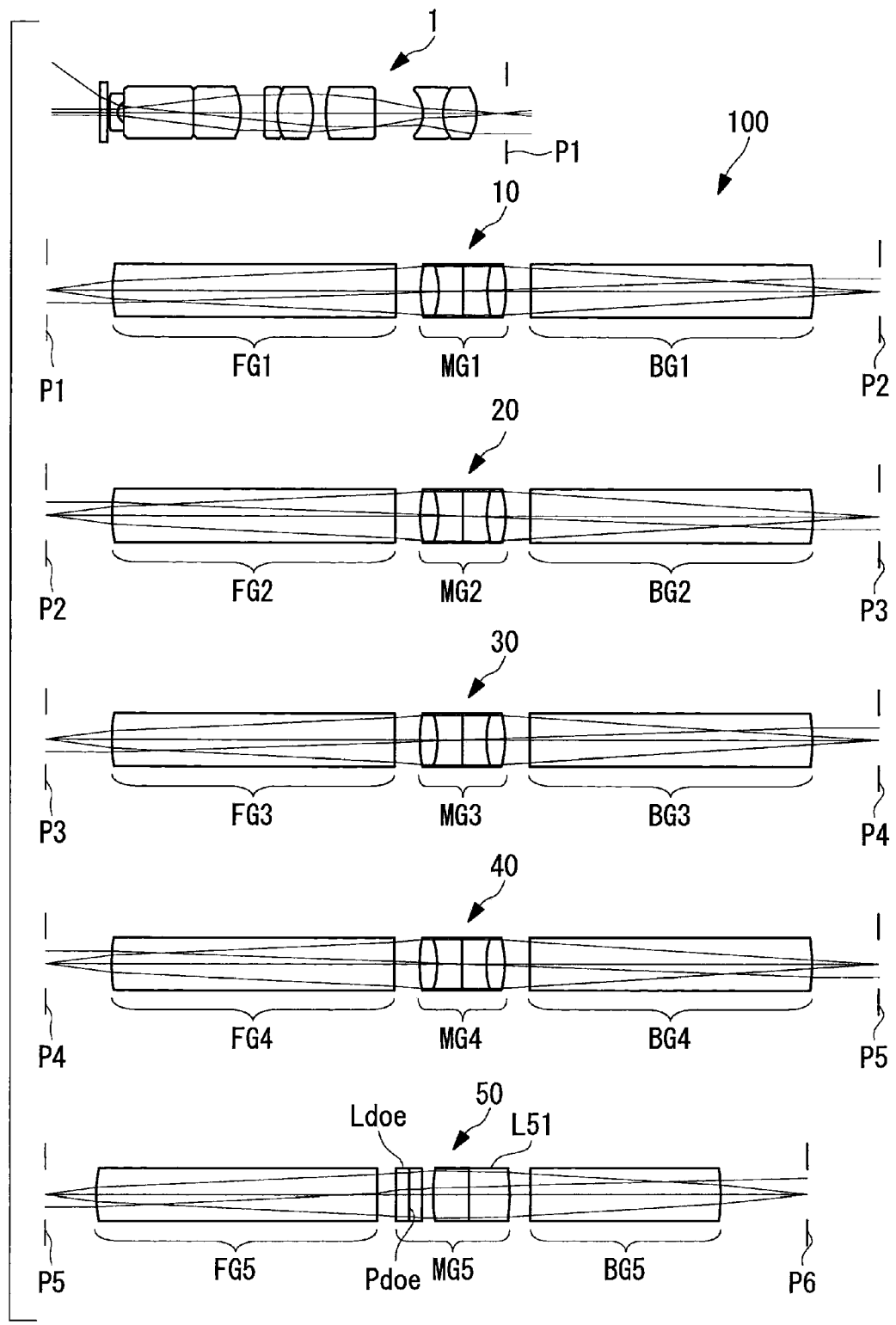
FIG. 1 is an overall configuration diagram of a rigid-scope optical system according to an embodiment of the present invention.
Figure 2:
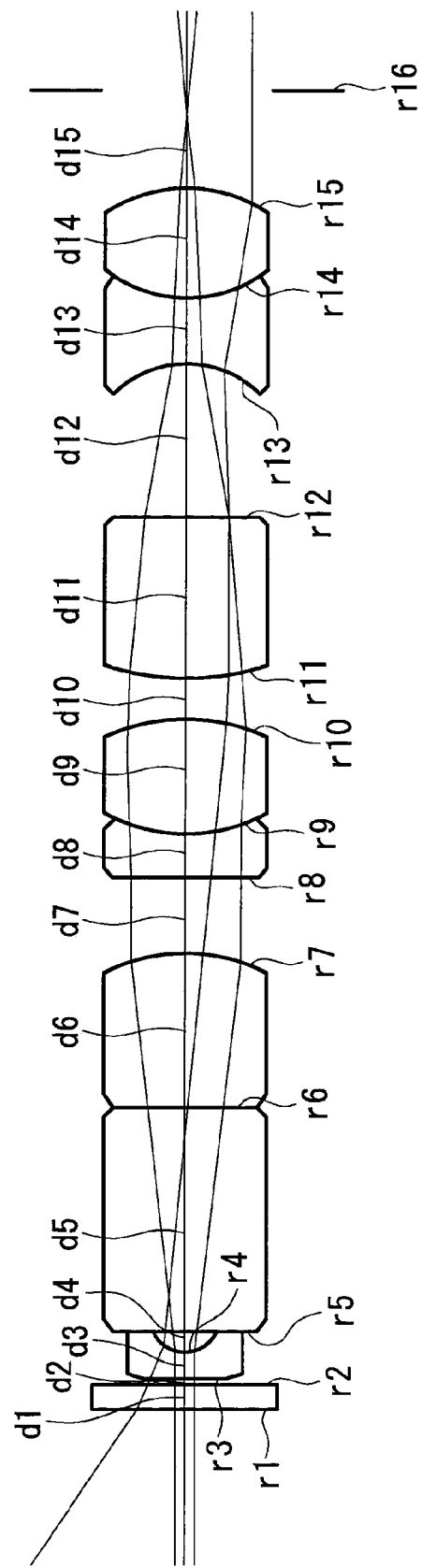
FIG. 2 is a lens diagram showing an objective optical system of a rigid-scope optical system according to Example 1 of the present invention.
Figure 3:
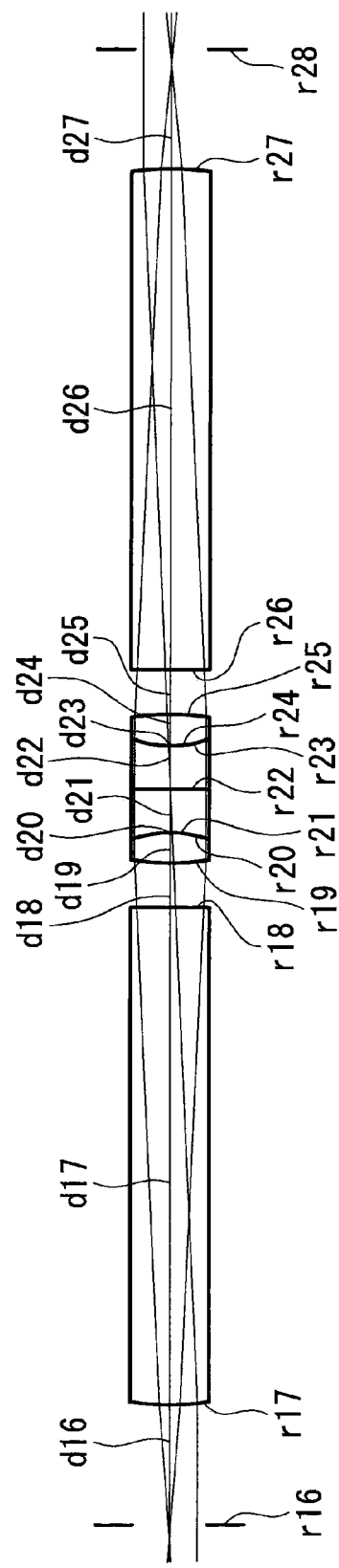
FIG. 3 is a lens diagram showing a first relay optical system of a rigid-scope optical system according to Example 1 of the present invention.
Figure 4:
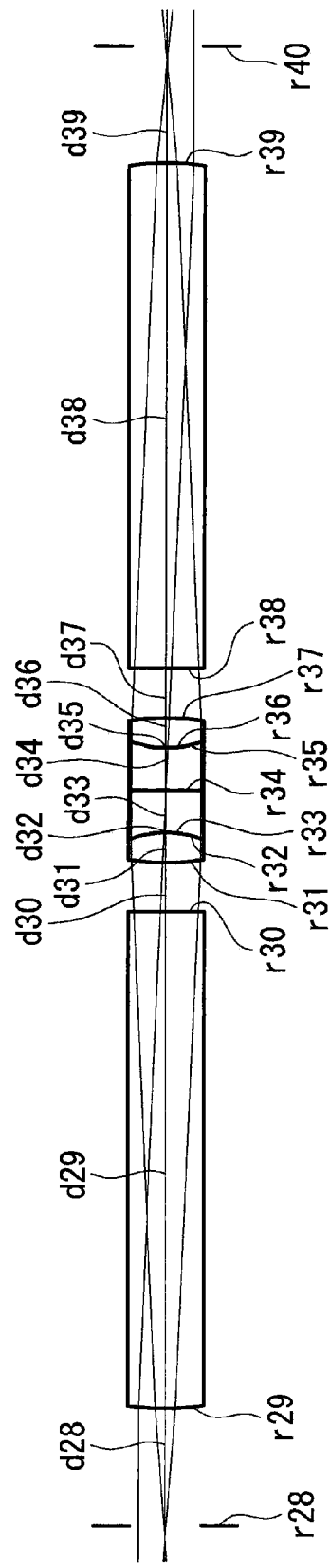
FIG. 4 is a lens diagram showing a second relay optical system of a rigid-scope optical system according to Example 1 of the present invention.
Figure 5:
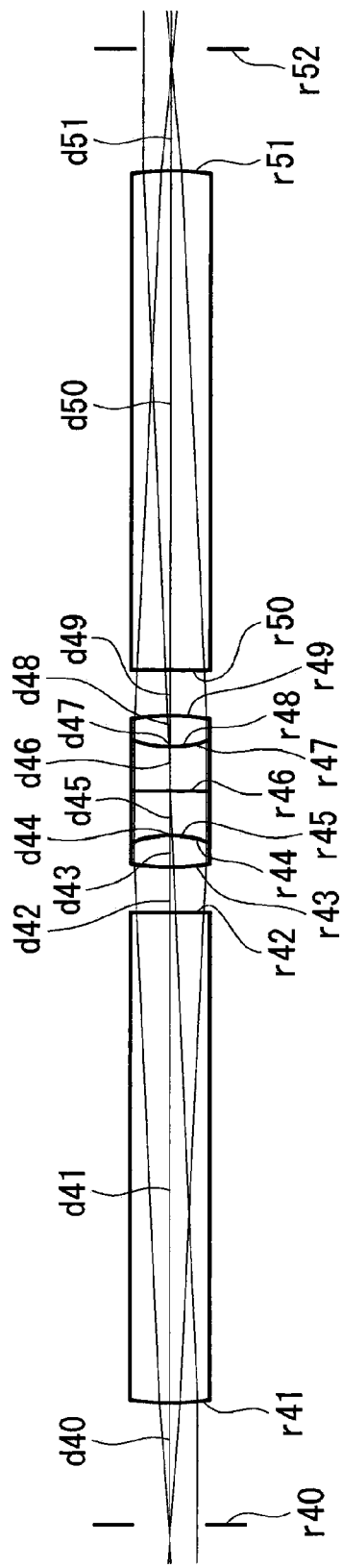
FIG. 5 is a lens diagram showing a third relay optical system of a rigid-scope optical system according to Example 1 of the present invention.
Figure 6:
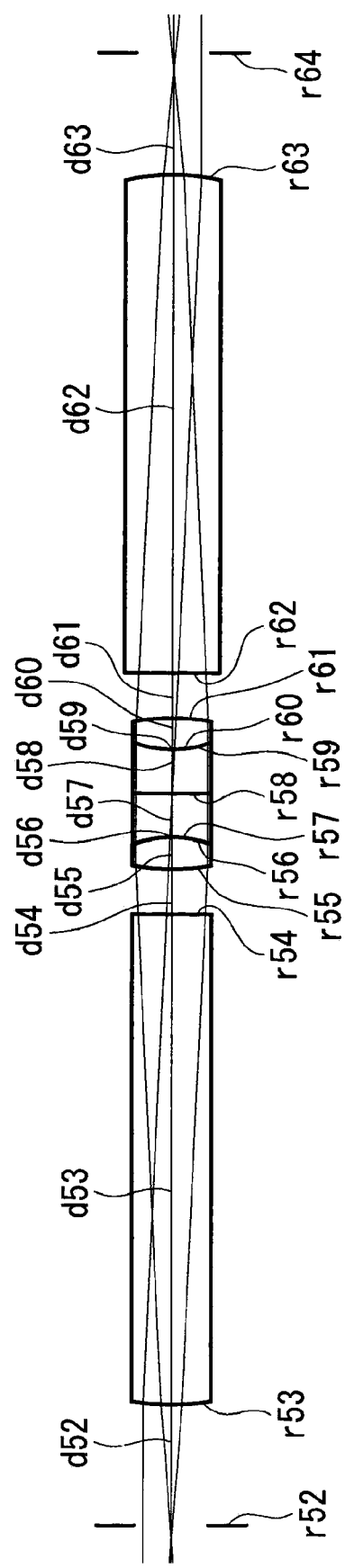
FIG. 6 is a lens diagram showing a fourth relay optical system of a rigid-scope optical system according to Example 1 of the present invention.
Figure 7:
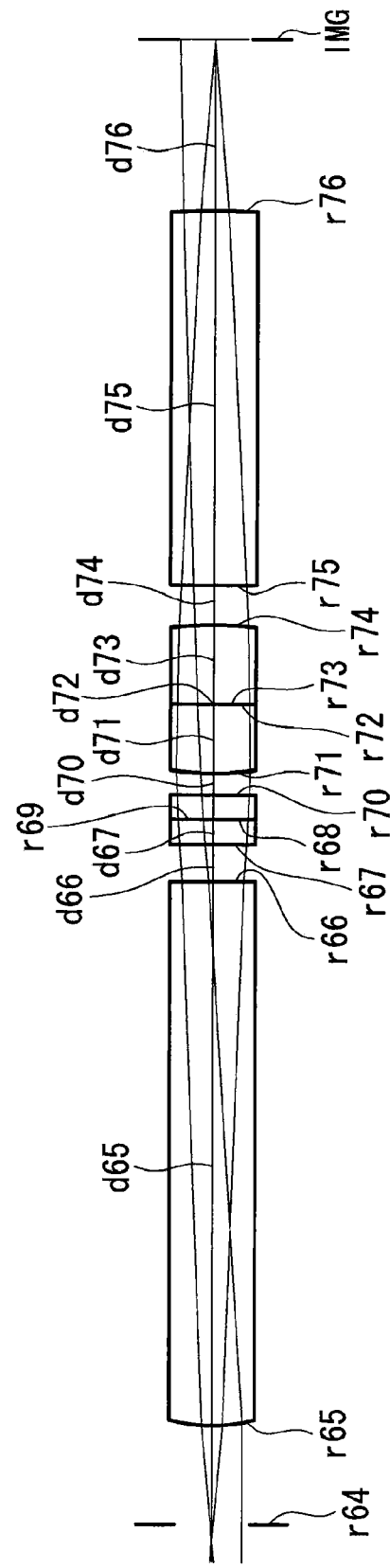
FIG. 7 is a lens diagram showing a fifth relay optical system of a rigid-scope optical system according to Example 1 of the present invention.

As shown in FIG. 1, the rigid-scope optical system 100 according to this embodiment is formed of an objective optical system 1 and first to fifth relay optical systems 10, 20, 30, 40, and 50. The rigid-scope optical system 100 is accommodated in a rigid, straight, cylindrical lens barrel such that the objective optical system 1 faces the tip side, and the rigid-scope optical system 100 transmits an optical image of an object that has been collected and imaged by the objective optical system 1 by means of repeated image formation by the first to fifth relay optical systems 10 to 50. The optical image that has been imaged by the fifth relay optical system 50 can be observed with an eyepiece optical system (not shown).

Here, although the objective optical system 1 and the first to fifth relay optical systems 10 to 50 are arranged on the same straight optical axis, for the sake of illustration in FIG. 1, the respective optical systems 1, 10, 20, 30, 40, and 50 are arranged by dividing the optical axis at respective imaging planes P1 to P5.

The objective optical system 1 collects the light from the object (not shown) and images it at the first imaging plane P1.

The first to fifth relay optical systems 10, 20, 30, 40, and 50 are respectively formed of positive front groups FG1 to FG5, positive middle groups MG1 to MG5, and positive back groups BG1 to BG5, in this order from the entrance side.

Specifically, the front groups FG1 to FG5 are formed of a single plano-convex lens whose convex surface faces the entrance side.

The back groups BG1 to BG5 are formed of a single plano-convex lens whose convex surface faces the exit side.

The middle groups MG1, MG2, MG3, and MG4 in the respective first to fourth relay optical systems 10, 20, 30, and 40 are each formed of a biconvex combined lens. The middle group MG5 in the fifth relay optical system (one of the relay optical systems) 50 is formed of a diffractive optical element Ldoe and a biconvex combined lens L51, which are described later.

The respective relay optical systems 10, 20, 30, 40, and 50 configured in this way relay the optical image on the first imaging plane P1 to the sixth imaging plane P6 at an optical magnification of substantially unity by imaging the optical images that have been imaged on the first to fifth imaging planes (primary imaging planes) P1 to P5 disposed at the immediately foregoing stages onto the second to sixth imaging planes (secondary imaging planes) P2 to P6 disposed at the immediately subsequent stages.

Here, the combined lens (combined optical system) provided in the first to fourth relay optical systems 10, 20, 30, and 40 is formed of a low-dispersion convex lens and a high-dispersion concave lens and corrects the axial chromatic aberration between two prescribed wavelengths, preferably between the C-line that corresponds to red (wavelength 656.3 nm) and the F-line that corresponds to blue (wavelength 486.1 nm), contained in the incident light beam.

The diffractive optical element Ldoe provided in the fifth relay optical system 50 is of the multilayer type. In other words, the diffractive optical element Ldoe is formed by combining two optical elements, which are formed of glass materials having different refractive indices and Abbe numbers from each other and have diffractive surfaces Pdoe at one of their surfaces such that the diffractive surfaces Pdoe face each other. The diffractive optical element Ldoe corrects the axial chromatic aberration related to another wavelength, preferably the e-line, which corresponds to green (546.1 nm), between the C-line and the F-line, contained in the light beam whose axial chromatic aberration between two wavelengths has been corrected in the first to fourth relay optical systems 10, 20, 30, and 40.

Here, the fifth relay optical system 50 satisfies the following expressions (1), (2), and (3):

$$3Lf < Lf\text{doe} \quad (1)$$

$$3Lb < Lb\text{doe} \quad (2)$$

$$0.5 < f\text{doe}/(ff+fm+fb) < 10 \quad (3)$$

where Lf is the distance from the fifth imaging plane (the primary imaging plane) to the surface at the extreme entrance side of the front group FG5, Lfdoe is the distance from the fifth imaging plane to the diffractive surface Pdoe, Lb is the distance from the surface at the extreme exit side of the back group BG5 to the sixth imaging plane (the secondary imaging plane), Lbdoe is the distance from the diffractive surface Pdoe to the sixth imaging plane, fdoe is the focal distance of the diffractive optical element Ldoe, ff is the focal distance of the front group FG5, fm is the focal distance of the middle group MG5, and fb is the focal distance of the back group BG5.

The expressions (1) and (2) define the position of the diffractive surface in the relay optical system. In other words, by positioning the diffractive surface sufficiently away from the front group surface at the extreme entrance side and back group surface at the extreme exit side, the light beam entering the diffractive surface becomes more collimated. Thus, it is possible to prevent the occurrence of flare at the diffractive surface with even higher reliability. When Lfdoe and Lbdoe are 3-times greater than Lf and LB, respectively, or less, it is difficult to sufficiently collimate the light beam entering the diffractive surface, and there is a risk of causing flare and a reduction in diffraction efficiency.

Expression (3) defines the power of the diffractive optical element relative to the power of the one relay optical system as a whole. In other words, by suitably setting a range of the relative power of the diffractive optical element, it is possible to suitably correct the axial chromatic aberration and to make the pitch of the diffraction grating, which is formed on the diffractive surface, have a size suitable for processing. When the value of expression (3) is 0.5 or less, the power distribution in the diffractive surface is increased, producing a negative secondary spectrum, and the pitch of the diffraction grating becomes small, making processing thereof difficult. On the other hand, when the value of expression (3) is 10 or more, the secondary spectrum cannot be corrected sufficiently, and in addition, the pitch on the diffractive surface is increased, causing the number of diffraction grating rulings within the effective diameter to be reduced, thereby reducing the diffraction efficiency.

With the thus-configured rigid-scope optical system 100, the secondary spectrum remaining from the first to fourth relay optical systems 10, 20, 30, and 40 is corrected by the diffractive optical element Ldoe that is provided in the fifth relay optical system 50. By doing so, it is possible to obtain an optical image whose axial chromatic aberration has been suitably corrected over the entire visible region at the sixth imaging plane P6.

In addition, in accordance with the expressions (1) and (2), the diffractive surface Pdoe is arranged at a position sufficiently away from the entrance side surface of the plano-convex lens in the front group FG5 and the exit side surface of the plano-convex lens in the back group BG5 in the fifth relay optical system 50; therefore, the light beam entering the diffractive surface Pdoe becomes a substantially collimated light beam. Thus, it is possible to achieve high diffraction efficiency at the diffractive surface Pdoe and to prevent the occurrence of flare. Furthermore, because the on-axis light beam and the off-axis light beam overlap at the position of the diffractive surface Pdoe, it is possible to prevent the occurrence of the magnification chromatic aberration and chromatic comatic aberration.

In addition, by setting the relative power of the diffractive surface Pdoe in the fifth relay optical system 50 to the level defined by expression (3), it is possible to suitably correct the secondary spectrum with the diffractive optical element Ldoe and also to make the pitch of the diffraction grating formed on the diffractive surface Pdoe so as to have a preferable size in terms of processability and diffraction efficiency. In addition, by configuring the middle group MG5 by combining the diffractive optical element Ldoe and the biconvex combined lens 51, it is possible to make the power distribution of the diffractive optical element Ldoe small.

EXAMPLE

Examples 1 to 4 of the rigid-scope optical system according to the above-mentioned embodiment of the present invention will be explained below with reference to FIGS. 2 to 15.

In the lens data described in each Example, r denotes the radius of curvature, d denotes the intersurface distance, ne denotes the refractive index for the e-line, and vd denotes the Abbe number for the d-line. The surface number corresponding to the aperture is assigned S, and the surface number corresponding to the diffractive surface is assigned P. In addition, in the lens data and the attached lens diagram, IMG denotes an image plane. With respect to the aspheric surface, the surface number in the lens data is shown with *, and the radius of paraxial curvature r, the conic coefficient k, and the aspheric coefficients Ai (i=2, 4, 6, 8, 10) of the aspheric surface shape, which are defined by the following expressions, are shown in the aspheric surface data. In the following expressions, the optical axis direction is defined as z, and the direction orthogonal to the optical axis is defined as y.

$$z = (y^2/r)/[1 + \{1 - (1+k)(y/r)^2\}^{1/2}] + A_2 y^2 + A_4 y^4 + A_6 y^6 + A_8 y^8 + A_{10} y^{10}$$

In addition, the diffractive surface is expressed as the aspheric surface shape of the equivalent ultra-high-index lens (refractive lens with very high refractive index) in accordance with the high-refractive-index method. The relationship according to the following expression, between the pitch d of the diffraction grating formed in the diffractive surface and the aspheric surface shape of the ultra-high-index lens, holds:

$$d = m\lambda/[(n-1)\{ch/(1 - c^2(1+k)h^2)^{1/2} + 2A_2 h + 4A_4 h^3 + 6A_6 h^5 + 8A_8 h^7 + 10A_{10} h^9 + \ldots \}]$$

where h is the ray height, and m is the diffraction order.

Example 1

As shown in FIGS. 2 to 7, the rigid-scope optical system according to Example 1 of the present invention is provided with the objective optical system and the first to fifth relay optical systems, in this order from the object side.

Each of the first to fourth relay optical systems is formed of the positive front group formed of the plano-convex lens whose convex surface faces the object side, the positive middle group formed of the combined lens, and the positive back group formed of the plano-convex lens whose convex surface faces the image side, in this order from the object side. The fifth relay optical system is formed of the positive front group formed of the plano-convex lens whose convex surface faces the object side, the positive middle group formed of the diffractive optical element and the combined lens, and the positive back group formed of the plano-convex lens whose convex surface faces the image side, in this order from the object side. The lens data for the rigid-scope optical system according to this Example is as follows.

Figure 8:
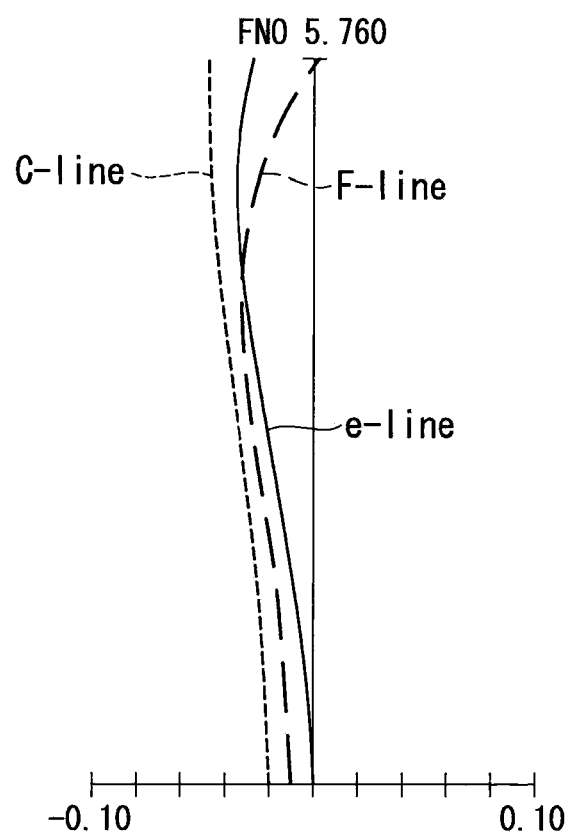
FIG. 8 is an axial chromatic aberration diagram of a rigid-scope optical system according to Example 1 of the present invention.

An axial chromatic aberration diagram of the thus-configured rigid-scope optical system is shown in FIG. 8. With the rigid-scope optical system of this Example, the axial chromatic aberration between the C-line and the F-line can be corrected by the combined lenses provided in the first to fourth relay optical systems, and the remaining axial chromatic aberration related to the e-line can be corrected by the diffractive optical element provided in the fifth relay optical system.

| Lens Data | | | | |
|---|---|---|---|---|
| Surface Number | r | d | ne | vd |
| 1 | ∞ | 0.1886 | 1.77066 | 71.79 |
| 2 | ∞ | 0.0613 | | |
| 3* | 22.2256 | 0.2358 | 1.79190 | 25.76 |
| 4 | 0.3320 | 0.1844 | | |
| 5 | ∞ | 1.9525 | 1.88814 | 40.78 |
| 6 | ∞ | 1.3205 | 1.88815 | 40.76 |
| 7 | −2.0440 | 0.6791 | | |
| 8 | 71.5633 | 0.3631 | 1.83932 | 37.16 |
| 9 | 1.8963 | 1.0140 | 1.48915 | 70.23 |
| 10 | −1.8963 | 0.3584 | | |
| 11 | 3.0373 | 1.3771 | 1.73234 | 54.68 |
| 12 | −115.0826 | 1.3205 | | |
| 13 | −0.9833 | 0.5565 | 1.85504 | 23.78 |
| 14 | 1.3960 | 0.9385 | 1.73234 | 54.68 |
| 15 | −1.3960 | 0.8348 | | |
| 16 | ∞ | 2.4429 | 1.00000 | |
| 17 | 4.9147 | 10.2057 | 1.59143 | 61.14 |
| 18 | ∞ | 0.9291 | | |
| 19 | 4.6600 | 0.6320 | 1.69661 | 53.21 |
| 20 | −2.4665 | 0.0024 | 1.51203 | 60.00 |
| 21 | −2.4625 | 0.8890 | 1.83945 | 42.72 |
| 22S | ∞ | 0.8890 | 1.83945 | 42.72 |
| 23 | 2.4625 | 0.0024 | 1.51203 | 60.00 |
| 24 | 2.4665 | 0.6320 | 1.69661 | 53.21 |
| 25 | −4.6600 | 0.9291 | | |
| 26 | ∞ | 10.2057 | 1.59143 | 61.14 |
| 27 | −4.9147 | 2.4429 | | |
| 28 | ∞ | 2.4429 | | |
| 29 | 4.9147 | 10.2057 | 1.59143 | 61.14 |
| 30 | ∞ | 0.9291 | | |
| 31 | 4.6600 | 0.6320 | 1.69661 | 53.21 |
| 32 | −2.4665 | 0.0024 | 1.51203 | 60.00 |
| 33 | −2.4625 | 0.8890 | 1.83945 | 42.72 |
| 34 | ∞ | 0.8890 | 1.83945 | 42.72 |
| 35 | 2.4625 | 0.0024 | 1.51203 | 60.00 |
| 36 | 2.4665 | 0.6320 | 1.69661 | 53.21 |
| 37 | −4.6600 | 0.9291 | | |
| 38 | ∞ | 10.2057 | 1.59143 | 61.14 |
| 39 | −4.9147 | 2.4429 | | |
| 40 | ∞ | 2.4429 | | |
| 41 | 4.9147 | 10.2057 | 1.59143 | 61.14 |
| 42 | ∞ | 0.9291 | | |
| 43 | 4.6600 | 0.6320 | 1.69661 | 53.21 |
| 44 | −2.4665 | 0.0024 | 1.51203 | 60.00 |
| 45 | −2.4625 | 0.8890 | 1.83945 | 42.72 |
| 46 | ∞ | 0.8890 | 1.83945 | 42.72 |
| 47 | 2.4625 | 0.0024 | 1.51203 | 60.00 |
| 48 | 2.4665 | 0.6320 | 1.69661 | 53.21 |
| 49 | −4.6600 | 0.9291 | | |
| 50 | ∞ | 10.2057 | 1.59143 | 61.14 |
| 51 | −4.9147 | 2.4429 | | |
| 52 | ∞ | 2.4429 | | |
| 53 | 4.9147 | 10.2057 | 1.59143 | 61.14 |
| 54 | ∞ | 0.9291 | | |
| 55 | 4.6600 | 0.6320 | 1.69661 | 53.21 |
| 56 | −2.4665 | 0.0024 | 1.51203 | 60.00 |
| 57 | −2.4625 | 0.8890 | 1.83945 | 42.72 |
| 58 | ∞ | 0.8890 | 1.83945 | 42.72 |
| 59 | 2.4625 | 0.0024 | 1.51203 | 60.00 |
| 60 | 2.4665 | 0.6320 | 1.69661 | 53.21 |
| 61 | −4.6600 | 0.9291 | | |
| 62 | ∞ | 10.2057 | 1.59143 | 61.14 |
| 63 | −4.9147 | 2.4429 | | |

-continued

Lens Data

| | | | | |
|---|---|---|---|---|
| 64 | ∞ | 1.8534 | | |
| 65 | 3.3539 | 10.1396 | 1.59143 | 61.14 |
| 66 | ∞ | 0.6980 | | |
| 67 | ∞ | 0.4716 | 1.64640 | 23.40 |
| 68P | 45347.1811 | 0.0000 | 930.00000 | −3.45 |
| 69 | ∞ | 0.4716 | 1.70455 | 36.40 |
| 70 | ∞ | 0.3867 | | |
| 71 | 8.2956 | 1.2734 | 1.83945 | 42.71 |
| 72 | ∞ | 0.0141 | | |
| 73 | ∞ | 1.4620 | 1.83945 | 42.71 |
| 74 | −10.6067 | 0.7499 | | |
| 75 | ∞ | 6.9044 | 1.48915 | 70.23 |
| 76 | −11.0870 | 3.1636 | | |
| IMG | ∞ | 0.0000 | | |

Aspheric Surface Data

Surface 3 k = 0.0000  $A_2 = 0$
$A_4 = 9.36E{-}01$  $A_6 = -1.84E{+}00$
$A_8 = 3.91E{+}00$  $A_{10} = 0.00E{+}00$

Surface 68 k = 24.0663  $A_2 = 0$
$A_4 = -2.30E{-}06$  $A_6 = 5.64E{-}07$
$A_8 = 1.88E{-}06$  $A_{10} = -7.55E{-}07$

Miscellaneous Data

| | |
|---|---|
| Object Distance | 14.1832 |
| Focal Distance | −1 |
| Image Height | 0.665 |
| Fno. | 5.76 |
| Viewing Angle | 70.71° |

Example 2

Figure 9:
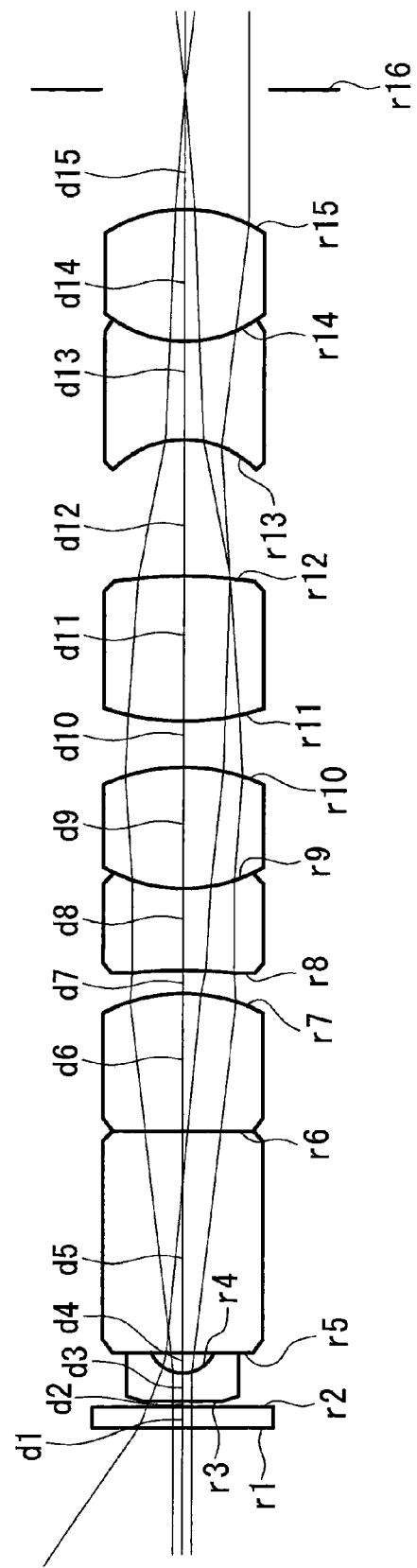
FIG. 9 is a lens diagram showing an objective optical system of a rigid-scope optical system according to Example 2 of the present invention.
Figure 10:
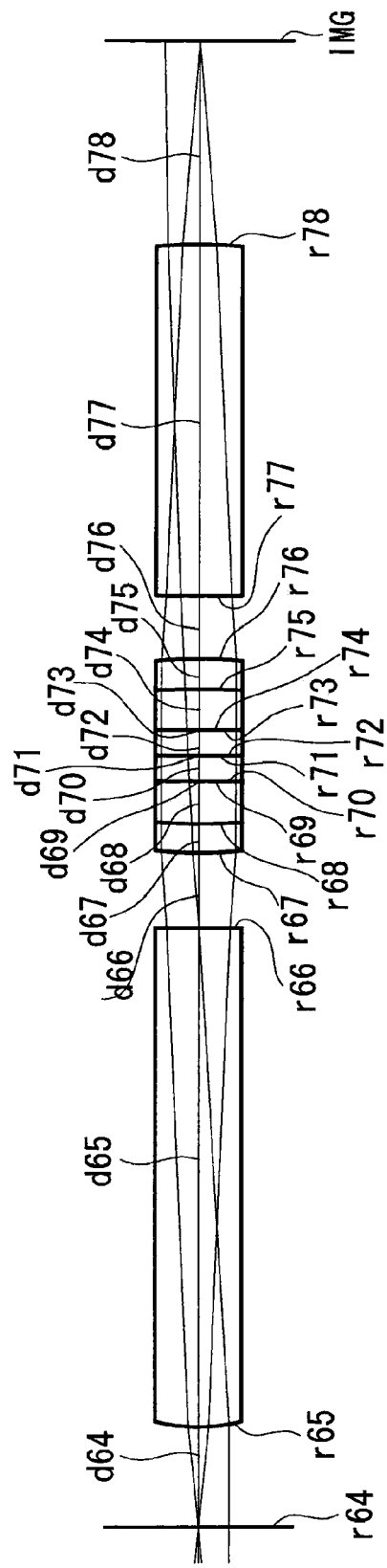
FIG. 10 is a lens diagram showing a fifth relay optical system of a rigid-scope optical system according to Example 2 of the present invention.

As shown in FIGS. 9 and 10, a rigid-scope optical system according to Example 2 of the present invention differs from the rigid-scope optical system of Example 1 mainly in the lens arrangements of the objective optical system (surface numbers 1 to 15) and the fifth relay optical system (surface numbers 65 to 78). In the fifth relay optical system, the diffractive optical element is flanked by the two combined lenses in the optical axis direction. The lens arrangements of the first to fourth relay optical systems are substantially the same as that of the rigid-scope optical system of Example 1, and an illustration thereof shall be omitted. The lens data for the rigid-scope optical system according to this Example is as follows.

Figure 11:
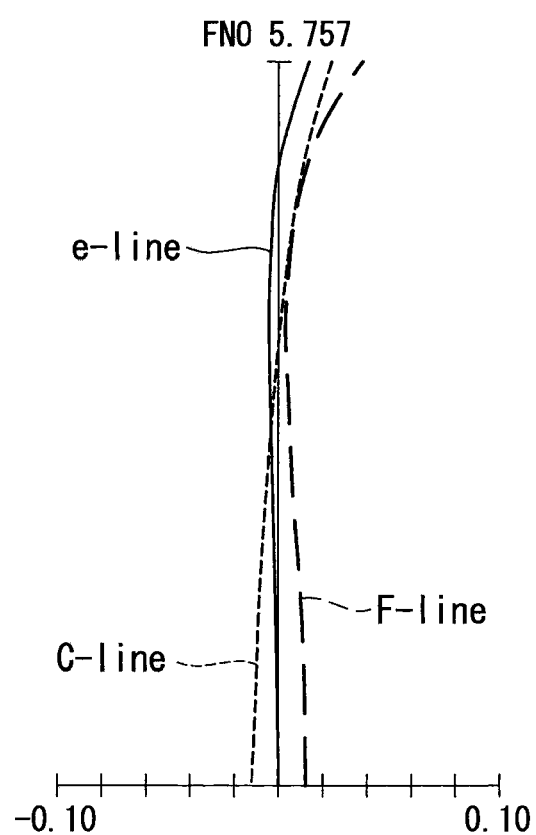
FIG. 11 is an axial chromatic aberration diagram of a rigid-scope optical system according to Example 2 of the present invention.

An axial chromatic aberration diagram of the thus-configured rigid-scope optical system is shown in FIG. 11. With the rigid-scope optical system of this Example, the axial chromatic aberration between the C-line and the F-line can be corrected by the combined lenses provided in the first to fourth relay optical systems, and the remaining axial chromatic aberration related to the e-line can be corrected by the diffractive optical element provided in the fifth relay optical system.

Lens Data

| Surface Number | r | d | ne | vd |
|---|---|---|---|---|
| 1 | ∞ | 0.1886 | 1.77066 | 71.79 |
| 2 | ∞ | 0.0613 | | |
| 3* | 22.2258 | 0.2358 | 1.79190 | 25.76 |
| 4 | 0.3315 | 0.1844 | | |
| 5 | ∞ | 1.9525 | 1.88814 | 40.78 |
| 6 | ∞ | 1.1936 | 1.88815 | 40.76 |
| 7 | −1.8699 | 0.2294 | | |
| 8 | −20.4710 | 0.7292 | 1.83932 | 37.16 |
| 9 | 1.9505 | 1.0468 | 1.48915 | 70.23 |
| 10 | −2.1435 | 0.4369 | | |
| 11 | 3.6510 | 1.2517 | 1.73234 | 54.68 |
| 12 | −4.8434 | 1.2162 | | |
| 13 | −1.1595 | 0.8772 | 1.85504 | 23.78 |
| 14 | 1.6194 | 1.1154 | 1.73234 | 54.68 |
| 15 | −1.8369 | 1.0399 | | |
| 16 | ∞ | 2.4430 | | |
| 17 | 4.9147 | 10.2058 | 1.59143 | 61.14 |
| 18 | ∞ | 0.9291 | | |
| 19 | 4.6601 | 0.6320 | 1.69661 | 53.21 |
| 20 | −2.4666 | 0.0024 | 1.51203 | 60.00 |
| 21 | −2.4625 | 0.8890 | 1.83945 | 42.72 |
| 22S | ∞ | 0.8890 | 1.83945 | 42.72 |
| 23 | 2.4625 | 0.0024 | 1.51203 | 60.00 |
| 24 | 2.4666 | 0.6320 | 1.69661 | 53.21 |
| 25 | −4.6601 | 0.9291 | | |
| 26 | ∞ | 10.2058 | 1.59143 | 61.14 |
| 27 | −4.9147 | 2.4430 | | |
| 28 | ∞ | 2.4430 | | |
| 29 | 4.9147 | 10.2058 | 1.59143 | 61.14 |
| 30 | ∞ | 0.9291 | | |
| 31 | 4.6601 | 0.6320 | 1.69661 | 53.21 |
| 32 | −2.4666 | 0.0024 | 1.51203 | 60.00 |
| 33 | −2.4625 | 0.8890 | 1.83945 | 42.72 |
| 34 | ∞ | 0.8890 | 1.83945 | 42.72 |
| 35 | 2.4625 | 0.0024 | 1.51203 | 60.00 |
| 36 | 2.4666 | 0.6320 | 1.69661 | 53.21 |
| 37 | −4.6601 | 0.9291 | | |
| 38 | ∞ | 10.2058 | 1.59143 | 61.14 |
| 39 | −4.9147 | 2.4430 | | |
| 40 | ∞ | 2.4430 | | |
| 41 | 4.9147 | 10.2058 | 1.59143 | 61.14 |
| 42 | ∞ | 0.9291 | | |
| 43 | 4.6601 | 0.6320 | 1.69661 | 53.21 |
| 44 | −2.4666 | 0.0024 | 1.51203 | 60.00 |
| 45 | −2.4625 | 0.8890 | 1.83945 | 42.72 |
| 46 | ∞ | 0.8890 | 1.83945 | 42.72 |
| 47 | 2.4625 | 0.0024 | 1.51203 | 60.00 |
| 48 | 2.4666 | 0.6320 | 1.69661 | 53.21 |
| 49 | −4.6601 | 0.9291 | | |
| 50 | ∞ | 10.2058 | 1.59143 | 61.14 |
| 51 | −4.9147 | 2.4430 | | |
| 52 | ∞ | 2.4430 | | |
| 53 | 4.9147 | 10.2058 | 1.59143 | 61.14 |
| 54 | ∞ | 0.9291 | | |
| 55 | 4.6601 | 0.6320 | 1.69661 | 53.21 |
| 56 | −2.4666 | 0.0024 | 1.51203 | 60.00 |
| 57 | −2.4625 | 0.8890 | 1.83945 | 42.72 |
| 58 | ∞ | 0.8890 | 1.83945 | 42.72 |
| 59 | 2.4625 | 0.0024 | 1.51203 | 60.00 |
| 60 | 2.4666 | 0.6320 | 1.69661 | 53.21 |
| 61 | −4.6601 | 0.9291 | | |
| 62 | ∞ | 10.2058 | 1.59143 | 61.14 |
| 63 | −4.9147 | 2.4430 | | |
| 64 | ∞ | 1.8865 | | |
| 65 | 3.7190 | 9.4128 | 1.59143 | 61.14 |
| 66 | ∞ | 1.4353 | | |
| 67 | 8.8488 | 0.5666 | 1.69661 | 53.21 |
| 68 | 15.2761 | 0.7759 | 1.83945 | 42.71 |
| 69 | ∞ | 0.0141 | | |
| 70 | ∞ | 0.4716 | 1.64640 | 23.40 |
| 71P | 56877.3621 | 0.0000 | 930.00000 | −3.45 |
| 72 | ∞ | 0.4716 | 1.70455 | 36.40 |
| 73 | ∞ | 0.0141 | | |
| 74 | ∞ | 0.7759 | 1.83945 | 42.71 |
| 75 | −15.2761 | 0.5666 | 1.69661 | 53.21 |
| 76 | −8.8488 | 1.2100 | | |
| 77 | ∞ | 6.6026 | 1.48915 | 70.23 |
| 78 | −7.9272 | 3.7871 | | |
| IMG | ∞ | 0.0000 | | |

-continued

Lens Data

Aspheric Surface Data

Surface 3

| | |
|---|---|
| k = 0 | $A_2 = 0$ |
| $A_4 = 9.36E-01$ | $A_6 = -1.84E+00$ |
| $A_8 = 3.91E+00$ | $A_{10} = 0.00E+00$ |

Surface 71

| | |
|---|---|
| k = 3.5108 | $A_2 = 0$ |
| $A_4 = -2.95E-06$ | $A_6 = 1.55E-06$ |
| $A_8 = 0.00E+00$ | $A_{10} = 0.00E+00$ |

Miscellaneous Data

| | |
|---|---|
| Object Distance | 14.1485 |
| Focal Distance | -1 |
| Image Height | 0.665 |
| Fno. | 5.7568 |
| Viewing Angle | 70.1° |

Example 3

Figure 12:
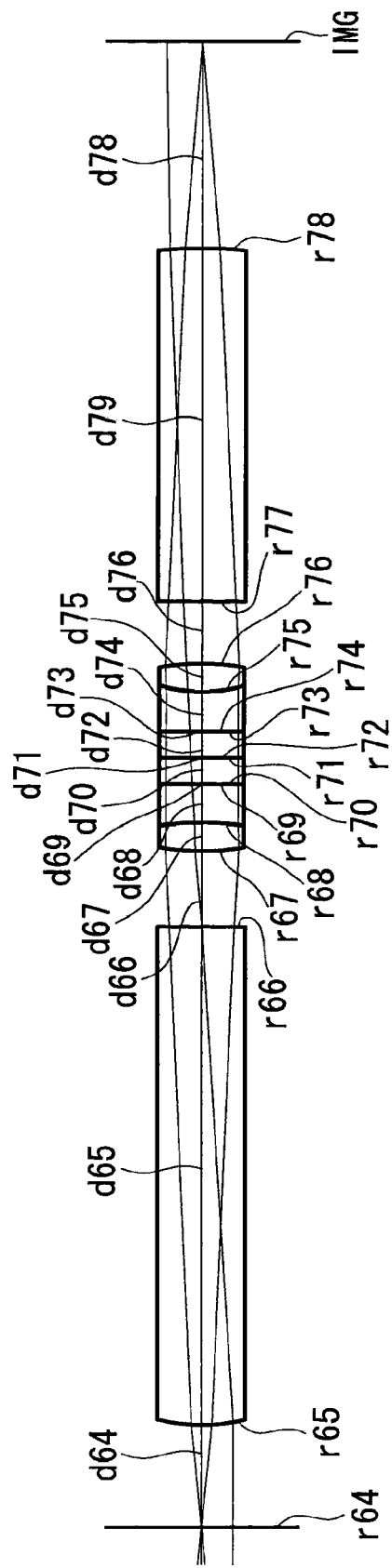
FIG. 12 is a lens diagram showing a fifth relay optical system of a rigid-scope optical system according to Example 3 of the present invention.

As shown in FIG. 12, a rigid-scope optical system according to Example 3 of the present invention differs from the rigid-scope optical system of Example 2 mainly in the lens arrangement of the fifth relay optical system (surface numbers 65 to 78). The lens arrangements of the objective optical system and the first to fourth relay optical systems are substantially the same as that of the rigid-scope optical system of Example 2, and an illustration thereof shall be omitted. The lens data for the rigid-scope optical system according to this Example is as follows.

Figure 13:
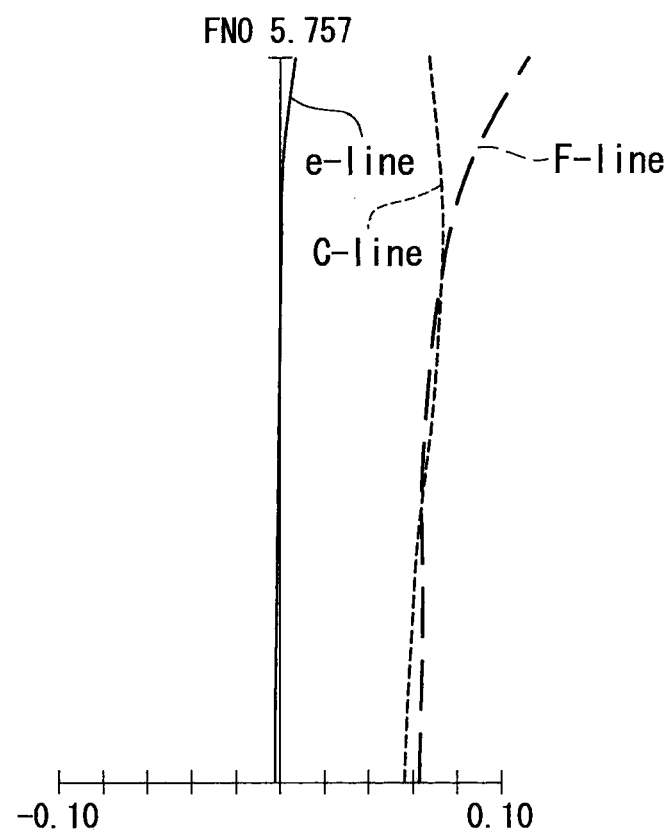
FIG. 13 is an axial chromatic aberration diagram of a rigid-scope optical system according to Example 3 of the present invention.

An axial chromatic aberration diagram of the thus-configured rigid-scope optical system is shown in FIG. 13. With the rigid-scope optical system of this Example, the axial chromatic aberration between the C-line and the F-line can be corrected by the combined lenses provided in the first to fourth relay optical systems, and the remaining axial chromatic aberration related to the e-line can be corrected by the diffractive optical element provided in the fifth relay optical system.

Lens Data

| Surface Number | r | d | ne | vd |
|---|---|---|---|---|
| 1 | ∞ | 0.1886 | 1.77066 | 71.79 |
| 2 | ∞ | 0.0613 | | |
| 3* | 22.2258 | 0.2358 | 1.79190 | 25.76 |
| 4 | 0.3315 | 0.1844 | | |
| 5 | ∞ | 1.9525 | 1.88814 | 40.78 |
| 6 | ∞ | 1.1936 | 1.88815 | 40.76 |
| 7 | -1.8699 | 0.2294 | | |
| 8 | -20.4710 | 0.7292 | 1.83932 | 37.16 |
| 9 | 1.9505 | 1.0468 | 1.48915 | 70.23 |
| 10 | -2.1435 | 0.4369 | | |
| 11 | 3.6510 | 1.2517 | 1.73234 | 54.68 |
| 12 | -4.8434 | 1.2162 | | |
| 13 | -1.1595 | 0.8772 | 1.85504 | 23.78 |
| 14 | 1.6194 | 1.1154 | 1.73234 | 54.68 |
| 15 | -1.8369 | 1.0399 | | |
| 16 | ∞ | 2.4430 | | |
| 17 | 4.9147 | 10.2058 | 1.59143 | 61.14 |
| 18 | ∞ | 0.9291 | | |
| 19 | 4.6601 | 0.6320 | 1.69661 | 53.21 |
| 20 | -2.4666 | 0.0024 | 1.51203 | 60.00 |
| 21 | -2.4625 | 0.8890 | 1.83945 | 42.72 |
| 22S | ∞ | 0.8890 | 1.83945 | 42.72 |
| 23 | 2.4625 | 0.0024 | 1.51203 | 60.00 |
| 24 | 2.4666 | 0.6320 | 1.69661 | 53.21 |
| 25 | -4.6601 | 0.9291 | | |
| 26 | ∞ | 10.2058 | 1.59143 | 61.14 |
| 27 | -4.9147 | 2.4430 | | |
| 28 | ∞ | 2.4430 | | |
| 29 | 4.9147 | 10.2058 | 1.59143 | 61.14 |
| 30 | ∞ | 0.9291 | | |
| 31 | 4.6601 | 0.6320 | 1.69661 | 53.21 |
| 32 | -2.4666 | 0.0024 | 1.51203 | 60.00 |
| 33 | -2.4625 | 0.8890 | 1.83945 | 42.72 |
| 34 | ∞ | 0.8890 | 1.83945 | 42.72 |
| 35 | 2.4625 | 0.0024 | 1.51203 | 60.00 |
| 36 | 2.4666 | 0.6320 | 1.69661 | 53.21 |
| 37 | -4.6601 | 0.9291 | | |
| 38 | ∞ | 10.2058 | 1.59143 | 61.14 |
| 39 | -4.9147 | 2.4430 | | |
| 40 | ∞ | 2.4430 | | |
| 41 | 4.9147 | 10.2058 | 1.59143 | 61.14 |
| 42 | ∞ | 0.9291 | | |
| 43 | 4.6601 | 0.6320 | 1.69661 | 53.21 |
| 44 | -2.4666 | 0.0024 | 1.51203 | 60.00 |
| 45 | -2.4625 | 0.8890 | 1.83945 | 42.72 |
| 46 | ∞ | 0.8890 | 1.83945 | 42.72 |
| 47 | 2.4625 | 0.0024 | 1.51203 | 60.00 |
| 48 | 2.4666 | 0.6320 | 1.69661 | 53.21 |
| 49 | -4.6601 | 0.9291 | | |
| 50 | ∞ | 10.2058 | 1.59143 | 61.14 |
| 51 | -4.9147 | 2.4430 | | |
| 52 | ∞ | 2.4430 | | |
| 53 | 4.9147 | 10.2058 | 1.59143 | 61.14 |
| 54 | ∞ | 0.9291 | | |
| 55 | 4.6601 | 0.6320 | 1.69661 | 53.21 |
| 56 | -2.4666 | 0.0024 | 1.51203 | 60.00 |
| 57 | -2.4625 | 0.8890 | 1.83945 | 42.72 |
| 58 | ∞ | 0.8890 | 1.83945 | 42.72 |
| 59 | 2.4625 | 0.0024 | 1.51203 | 60.00 |
| 60 | 2.4666 | 0.6320 | 1.69661 | 53.21 |
| 61 | -4.6601 | 0.9291 | | |
| 62 | ∞ | 10.2058 | 1.59143 | 61.14 |
| 63 | -4.9147 | 2.4430 | | |
| 64 | ∞ | 1.8865 | | |
| 65 | 3.7190 | 9.4128 | 1.59143 | 61.14 |
| 66 | ∞ | 1.4135 | | |
| 67 | 4.7493 | 0.5333 | 1.69661 | 53.21 |
| 68 | -2.6933 | 0.7447 | 1.83945 | 42.71 |
| 69 | ∞ | 0.0141 | | |
| 70 | ∞ | 0.4716 | 1.64640 | 23.40 |
| 71P | 231984.5611 | 0.0000 | 930.00000 | -3.45 |
| 72 | ∞ | 0.4716 | 1.70455 | 36.40 |
| 73 | ∞ | 0.0141 | | |
| 74 | ∞ | 0.7447 | 1.83945 | 42.71 |
| 75 | 2.6933 | 0.5333 | 1.69661 | 53.21 |
| 76 | -4.7493 | 1.1610 | | |
| 77 | ∞ | 6.6026 | 1.48915 | 70.23 |
| 78 | -7.9272 | 3.8241 | | |
| IMG | ∞ | 0.0000 | | |

Aspheric Surface Data

Surface 3

| | |
|---|---|
| k = 0.0000 | $A_2 = 0$ |
| $A_4 = 9.36E-01$ | $A_6 = -1.84E+00$ |
| $A_8 = 3.91E+00$ | $A_{10} = 0.00E+00$ |

Surface 71

| | |
|---|---|
| k = 3.5112 | $A_2 = 0$ |
| $A_4 = -3.19E-06$ | $A_6 = 2.50E-06$ |
| $A_8 = 0.00E+00$ | $A_{10} = 0.00E+00$ |

Miscellaneous Data

| | |
|---|---|
| Object Distance | 14.1485 |
| Focal Distance | -1 |
| Image Height | 0.665 |

-continued

| Lens Data | | |
|---|---|---|
| Fno. | 5.7568 | |
| Viewing Angle | 69.98° | |

Example 4

Figure 14:
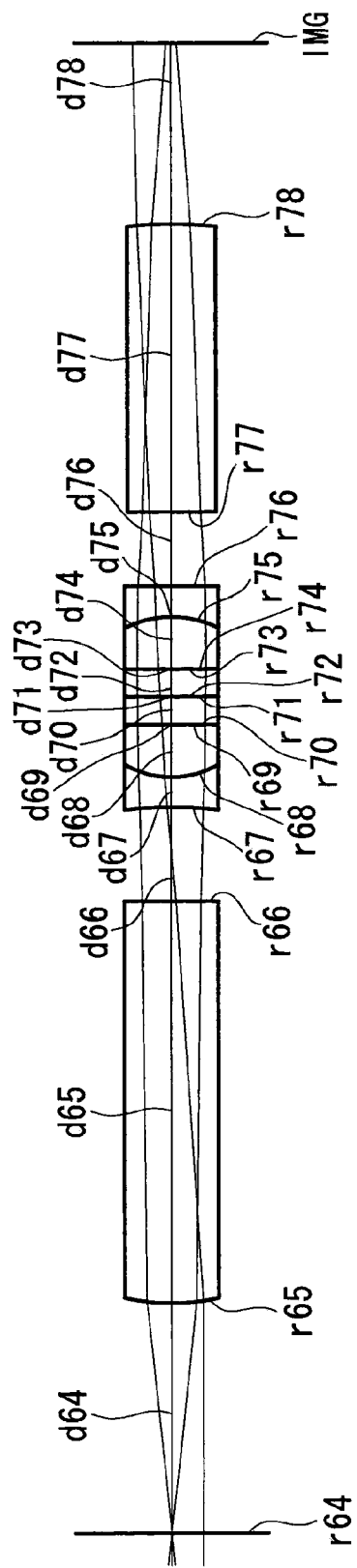
FIG. 14 is a lens diagram showing a fifth relay optical system of a rigid-scope optical system according to Example 4 of the present invention.

As shown in FIG. 14, a rigid-scope optical system according to Example 4 of the present invention differs from the rigid-scope optical system of Example 2 mainly in the lens arrangement of the fifth relay optical system (surface numbers 65 to 78). The arrangements of the objective optical system and the first to fourth relay optical systems are substantially the same as that of the rigid-scope optical system of Example 2, and an illustration thereof shall be omitted. The lens data for the rigid-scope optical system according to this Example is as follows.

Figure 15:
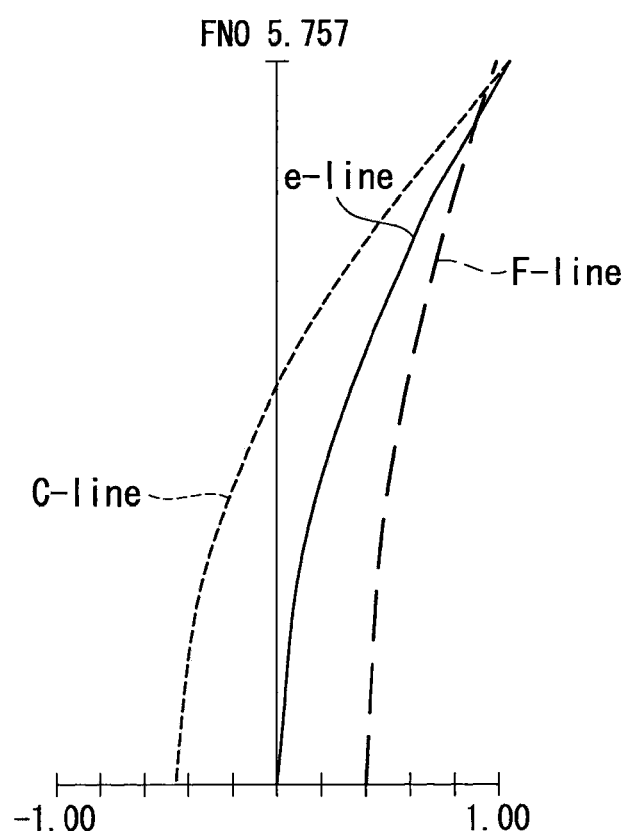
FIG. 15 is an axial chromatic aberration diagram of a rigid-scope optical system according to Example 4 of the present invention.

An axial chromatic aberration diagram of the thus-configures rigid-scope optical system is shown in FIG. 15. With the rigid-scope optical system of this Example, the axial chromatic aberration between the C-line and the F-line can be corrected by the combined lenses provided in the first to fourth relay optical systems, and the remaining axial chromatic aberration related to the e-line can be corrected by the diffractive optical element provided in the fifth relay optical system.

| Lens Data | | | | |
|---|---|---|---|---|
| Surface Number | r | d | ne | νd |
| 1 | ∞ | 0.1886 | 1.77066 | 71.79 |
| 2 | ∞ | 0.0613 | | |
| 3* | 22.2256 | 0.2358 | 1.79190 | 25.76 |
| 4 | 0.3315 | 0.1844 | | |
| 5 | ∞ | 1.9525 | 1.88814 | 40.78 |
| 6 | ∞ | 1.1936 | 1.88815 | 40.76 |
| 7 | −1.8699 | 0.2294 | | |
| 8 | −20.4708 | 0.7292 | 1.83932 | 37.16 |
| 9 | 1.9504 | 1.0468 | 1.48915 | 70.23 |
| 10 | −2.1435 | 0.4369 | | |
| 11 | 3.6510 | 1.2517 | 1.73234 | 54.68 |
| 12 | −4.8433 | 1.2162 | | |
| 13 | −1.1595 | 0.8772 | 1.85504 | 23.78 |
| 14 | 1.6194 | 1.1154 | 1.73234 | 54.68 |
| 15 | −1.8368 | 1.0399 | | |
| 16 | ∞ | 2.4429 | | |
| 17 | 4.9147 | 10.2057 | 1.59143 | 61.14 |
| 18 | ∞ | 0.9291 | | |
| 19 | 4.6600 | 0.6320 | 1.69661 | 53.21 |
| 20 | −2.4665 | 0.0024 | 1.51203 | 60.00 |
| 21 | −2.4625 | 0.8890 | 1.83945 | 42.72 |
| 22S | ∞ | 0.8890 | 1.83945 | 42.72 |
| 23 | 2.4625 | 0.0024 | 1.51203 | 60.00 |
| 24 | 2.4665 | 0.6320 | 1.69661 | 53.21 |
| 25 | −4.6600 | 0.9291 | | |
| 26 | ∞ | 10.2057 | 1.59143 | 61.14 |
| 27 | −4.9147 | 2.4429 | | |
| 28 | ∞ | 2.4429 | | |
| 29 | 4.9147 | 10.2057 | 1.59143 | 61.14 |
| 30 | ∞ | 0.9291 | | |
| 31 | 4.6600 | 0.6320 | 1.69661 | 53.21 |
| 32 | −2.4665 | 0.0024 | 1.51203 | 60.00 |
| 33 | −2.4625 | 0.8890 | 1.83945 | 42.72 |
| 34 | ∞ | 0.8890 | 1.83945 | 42.72 |
| 35 | 2.4625 | 0.0024 | 1.51203 | 60.00 |
| 36 | 2.4665 | 0.6320 | 1.69661 | 53.21 |
| 37 | −4.6600 | 0.9291 | | |
| 38 | ∞ | 10.2057 | 1.59143 | 61.14 |
| 39 | −4.9147 | 2.4429 | | |

-continued

| Lens Data | | | | |
|---|---|---|---|---|
| 40 | ∞ | 2.4429 | | |
| 41 | 4.9147 | 10.2057 | 1.59143 | 61.14 |
| 42 | ∞ | 0.9291 | | |
| 43 | 4.6600 | 0.6320 | 1.69661 | 53.21 |
| 44 | −2.4665 | 0.0024 | 1.51203 | 60.00 |
| 45 | −2.4625 | 0.8890 | 1.83945 | 42.72 |
| 46 | ∞ | 0.8890 | 1.83945 | 42.72 |
| 47 | 2.4625 | 0.0024 | 1.51203 | 60.00 |
| 48 | 2.4665 | 0.6320 | 1.69661 | 53.21 |
| 49 | −4.6600 | 0.9291 | | |
| 50 | ∞ | 10.2057 | 1.59143 | 61.14 |
| 51 | −4.9147 | 2.4429 | | |
| 52 | ∞ | 2.4429 | | |
| 53 | 4.9147 | 10.2057 | 1.59143 | 61.14 |
| 54 | ∞ | 0.9291 | | |
| 55 | 4.6600 | 0.6320 | 1.69661 | 53.21 |
| 56 | −2.4665 | 0.0024 | 1.51203 | 60.00 |
| 57 | −2.4625 | 0.8890 | 1.83945 | 42.72 |
| 58 | ∞ | 0.8890 | 1.83945 | 42.72 |
| 59 | 2.4625 | 0.0024 | 1.51203 | 60.00 |
| 60 | 2.4665 | 0.6320 | 1.69661 | 53.21 |
| 61 | −4.6600 | 0.9291 | | |
| 62 | ∞ | 10.2057 | 1.59143 | 61.14 |
| 63 | −4.9147 | 2.4429 | | |
| 64 | ∞ | 4.0000 | | |
| 65 | 3.1973 | 7.0000 | 1.59143 | 61.14 |
| 66 | ∞ | 1.6210 | | |
| 67 | −6.9788 | 0.5202 | 1.69661 | 53.21 |
| 68 | 1.6001 | 0.9080 | 1.83945 | 42.71 |
| 69 | ∞ | 0.0141 | | |
| 70 | ∞ | 0.4716 | 1.64640 | 23.40 |
| 71P | 12138.3807 | 0.0000 | 930.00000 | −3.45 |
| 72 | ∞ | 0.4716 | 1.70455 | 36.40 |
| 73 | ∞ | 0.0141 | | |
| 74 | ∞ | 0.9039 | 1.83945 | 42.71 |
| 75 | −1.4289 | 0.5190 | 1.69661 | 53.21 |
| 76 | 31.4292 | 1.3000 | | |
| 77 | ∞ | 4.9223 | 1.48915 | 70.23 |
| 78 | −5.7900 | 3.1223 | | |
| IMG | ∞ | 0.0000 | | |

| Aspheric Surface Data | |
|---|---|
| Surface 3 | |
| k = 0.0000 | $A_2 = 0$ |
| $A_4$ = 9.36E−01 | $A_6$ = −1.84E+00 |
| $A_8$ = 3.91E+00 | $A_{10}$ = 0.00E+00 |
| Surface 71 | |
| k = 0.00E+00 | $A_2 = 0$ |
| $A_4$ = −3.64E−05 | $A_6$ = 3.65E−06 |
| $A_8$ = 0.00E+00 | $A_{10}$ = 0.00E+00 |

| Miscellaneous Data | |
|---|---|
| Object Distance | 14.1483 |
| Focal Distance | −1 |
| Image Height | 0.665 |
| Fno. | 5.7568 |
| Viewing Angle | 69.51° |

Respective values of the parameters in the conditional expressions (1), (2), and (3) for the fifth relay optical system provided in the rigid-scope optical system according to above-mentioned Examples 1 to 4 are as shown in Table 1.

TABLE 1

| | Conditional Expression | Example 1 | Example 2 | Example 3 | Example 4 |
|---|---|---|---|---|---|
| (1) | 3Lf | 5.560 | 5.660 | 5.660 | 12.000 |
| | Lfdoe | 13.163 | 14.563 | 14.476 | 14.535 |

TABLE 1-continued

|  | Conditional Expression | Example 1 | Example 2 | Example 3 | Example 4 |
|---|---|---|---|---|---|
| (2) | 3Lb | 9.491 | 11.361 | 11.472 | 9.367 |
|  | Lbdoe | 14.426 | 13.428 | 13.351 | 11.253 |
| (3) | fdoe | 48.827 | 61.241 | 249.784 | 13.070 |
|  | ff | 5.670 | 6.288 | 6.288 | 5.406 |
|  | fm | 5.433 | 5.763 | 5.763 | 6.712 |
|  | fb | 22.666 | 16.206 | 16.206 | 11.837 |
|  | fdoe/(ff + fm + fb) | 1.446 | 2.167 | 8.840 | 0.546 |

{Reference Signs List}

| | |
|---|---|
| 1 | objective optical system |
| 10, 20, 30, 40, 50 | relay optical system |
| 100 | rigid-scope optical system |
| BG1, BG2, BG3, BG4, BG5 | back group |
| MG1, MG2, MG3, MG4, MG5 | middle group |
| FG1, FG2, FG3, FG4, FG5 | front group |
| Ldoe | diffractive optical element |
| P1, P2, P3, P4, P5, P6 | imaging plane |
| Pdoe | diffractive surface |

The invention claimed is:

1. A rigid-scope optical system comprising:
an objective optical system; and
a plurality of relay optical systems that relay an optical image imaged at a primary imaging plane at the entrance side onto a secondary imaging plane at an exit side;
wherein each of the plurality of relay optical systems is formed of a positive front group, a middle group, and a back group in this order from an entrance side,
wherein the middle group of one of the relay optical systems that is disposed at an extreme exit side is provided with a diffractive optical element having a diffractive surface,
and wherein the diffractive optical element receives an incident light beam, at the diffractive surface, whose axial chromatic aberration between at least two wavelengths has been corrected by an optical system other than the diffractive optical element, and the diffractive optical element corrects axial chromatic aberration related to another wavelength contained in the light beam.

2. The rigid-scope optical system according to claim 1, wherein the relay optical system disposed at an extreme exit side satisfies the following expressions (1) and (2):

$$3Lf < Lf\text{doe} \quad (1)$$

$$3Lb < Lb\text{doe} \quad (2)$$

where
Lf is a distance from a primary imaging plane to a surface at the extreme entrance side of the front group of the relay optical system disposed at an extreme exit side,
Lfdoe is a distance from the primary imaging plane to the diffractive surface of the relay optical system disposed at an extreme exit side,
Lb is a distance from a surface at the extreme exit side of the back group to a secondary imaging plane of the relay optical system disposed at an extreme exit side, and
Lbdoe is a distance from the diffractive surface to the secondary imaging plane of the relay optical system disposed at an extreme exit side.

3. The rigid-scope optical system according to claim 1, wherein the relay optical system disposed at an extreme exit side satisfies the following expression (3):

$$0.5 < f\text{doe}/(ff+fm+fb) < 10 \quad (3)$$

where
fdoe is a focal distance of the diffractive optical element,
ff is a focal distance of the front group of the relay optical system disposed at an extreme exit side,
fm is a focal distance of the middle group of the relay optical system disposed at an extreme exit side, and
fb is a focal distance of the back group of the relay optical system disposed at an extreme exit side.

4. The rigid-scope optical system according to claim 1, wherein the relay optical system disposed at an extreme exit side or/and other relay optical systems comprises/comprise at least one combined optical system.

5. A rigid endoscope comprising the rigid-scope optical system according to claim 1.

* * * * *